United States Patent [19]

Charkoudian

[11] Patent Number: 4,877,454

[45] Date of Patent: Oct. 31, 1989

[54] MODEL HUMAN SKIN

[75] Inventor: John C. Charkoudian, Newton, Mass.

[73] Assignee: The Kendall Company, Boston, Mass.

[21] Appl. No.: 152,212

[22] Filed: Feb. 4, 1988

[51] Int. Cl.$^4$ ............................................. C08L 89/04
[52] U.S. Cl. ..................................... 106/131; 106/132; 106/124; 106/159; 428/15; 623/15; 446/385
[58] Field of Search ................... 428/15; 106/131, 132, 106/159, 124; 623/15; 446/385

[56] References Cited

U.S. PATENT DOCUMENTS 3,655,416  4/1972  Vinson et al. ....................... 106/155

OTHER PUBLICATIONS

Grant & Hackh's Chemical Dictionary, 5th Ed., p. 340 Lipid, Lipoid, (1987) diglyceride p. 185.

Hawley's Condensed Chemical Dictionary, 11th Ed., p. 507 fatty acid; triglyceride p. 1183; p. 704 lipid.
Webster's II New Riverside University Dictionary, p. 697 lipid; p. 467 fatty acid.

*Primary Examiner*—Joseph L. Schofer
*Assistant Examiner*—John J. Guarriello
*Attorney, Agent, or Firm*—Alvin Isaacs

[57] ABSTRACT

Model skin surface adapted for testing adhesion of medical adhesives as a screening test and/or as an alternative to costly and highly variable human skin substrates, which model skin possesses human topography and consists essentially of a water content which is adjustable to simulate varying moisture contents in human skin; water-swellable but water-insoluble proteinaceous material; and fatty acid di- or triglyceride.

10 Claims, No Drawings

MODEL HUMAN SKIN

BACKGROUND OF THE INVENTION

The development and evaluation of pressure-sensitive adhesive tapes for medical use, e.g. so-called medical adhesives such as would be employed to hold a wound dressing in place, involve complex issues in adhesion to skin and related testing procedures.

Although human test panels will of course provide in vivo data, these test procedures are costly and difficult, and are characterized by large variability in such factors as surface morphology, presence of surface moisture and sebum, etc. Moreover, protocol for human testing requires screening for pregnancy, medical problems including any which may be affected by transdermal diffusion of trace amounts of unreacted monomer which may be present in the adhesive formulation, filling out and signing consent forms, liability issues and the like.

On the other hand, in vitro methods using excised human skin and animal models are also highly variable, tedious and preparation intensive. Other test substrates, such as steel and glass, offer ease and precision in laboratory testing, but the test results are not easily correlated to the results obtainable in the contemplated use on actual skin surfaces.

For these reasons, it has heretofore been suggested that in vitro testing be done on smooth polyamide surfaces of collagen and 66-nylon. (See, for example, Komerska, J. F. and Moffett, N., *Proceedings of Pressure Sensitive Tape Council*, 108 (1985); Schott, H., J. Pharm. Sci., 60, 1894 (1971). However, these materials are inadequate for analytical comparison with the dispersive and polar intermolecular properties of human skin. Moreover, they do not account for the topographical aspects, including variations thereof, in human skin.

In view of the foregoing discussion it will be appreciated that there is a great need by manufacturers of medical adhesives and tapes, as well as other investigators of their application to the skin, for inexpensive, reproducible test surfaces whose properties substantially correlate to or reflect those of human skin.

BRIEF DESCRIPTION OF THE INVENTION

In accordance with the present invention, this task is solved in an elegant manner by providing a model skin, one surface of which possesses human skin topography, the model skin being a water-swellable, water-insoluble proteinaceous matrix consisting essentially of:

(1) water in an adjustable amount ranging from about 8 percent to about 45 percent by weight based upon the total weight of the matrix;

(2) water-soluble proteinaceous material which has been crosslinked to render it water-insoluble and water-swellable; and (3) di- or triglyceridic ester of a fatty acid containing at least twelve carbon atoms in the fatty acid chain (a $C_{12}$ or greater higher fatty acid), or a substituted derivative thereof, the crosslinked proteinaceous material and glyceridic ester constituting the remaining percentage of essential material in said matrix, the ratio by weight of the proteinaceous material to glyceridic ester being from about 2:1 to about 4:1, and preferably from about 3:1 to about 3.5:1.

DETAILED DESCRIPTION OF THE INVENTION

Skin is a complex, organized structure composed primarily of protein, lipid and water. The outermost layer, the nonviable epidermis or stratum corneum, has a normal water content of about 25% of its dry weight. This percentage may increase to greater than 75% under conditions of hydration. This already intricate arrangement is further complicated by the elevations and depressions resulting in the topography of human skin.

In accordance with the present invention, therefore, a desirable test material should contain a protein and a glyceridic ester (lipid) as heretofore defined along with an adjustable water content. Moreover, the test surface should incorporate the topographical aspects of human skin.

As heretofore mentioned, the model skin of this invention possesses human skin topography and consists essentially of water, crosslinked proteinaceous material and fatty acid triglyceride in the amounts previously set forth in the "Brief Description of the Invention".

While the ratio of protein to triglyceride remains constant within the prescribed ratio, the water content is adjustable at will by the clinician within the recited range in order to simulate varying moisture contents of human skin for screening tests over such a variety of contemplated human use.

As examples of suitable water-soluble protein for preparing the model skin, mention may be made of albumin from animal tissue, gelatin such as porcine or calf skin gelatin being particularly efficacious. Other useful proteinaceous materials include soluble collagent, soluble borine globulins, polylysine, polyamino acid copolymers and terpolymers, etc.

Crosslinking may be effected in per se known manner utilizing conventional crosslinking agents for this purpose, formaldehyde being illustrative. Other per se known reagents for this purpose include glataraldehyde and succinaldehyde.

In general, the degree of crosslinking will be substantially complete in order to convert the water-soluble gelatin or other protein to a water-swellable but water-insoluble proteinaceous matrix.

However, as will be appreciated by those skilled in the art, crosslinking should not be so complete that the kinetics are so rapid that they preclude the coating process to form the model skin matrix. In general, a degree of crosslinking not exceeding abuut 95 percent is suitable.

As examples of suitable glyceridicesters, mention may be made of the di- or triglycerides of lauric, myristic, palmitic, stearic and oleic acid, including substituted derivatives thereof. Preferred are the triglycerides.

A particularly useful triglyceride is

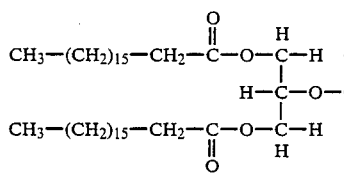 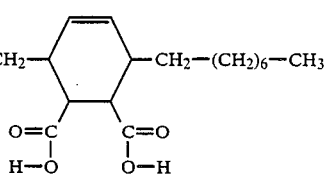

2-(alkoyloxy)-1-[(alkoyloxy)methyl]-ethyl-7-(4-heptyl-5,6-dicarboxy-2-cyclohexane-1-yl)heptanoate hereinafter simply referred to as "G2".

The model skin formulation may and typically will contain other reagents performing specific desired functions.

For instance, unless the formulation is to be used shortly after preparation and then discarded, it should contain an effective amount (e.g. less than one percent by weight) of a bacterial growth inhibitor.

It should also contain an effective amount of a reagent to prevent phase separation, e.g. an alkali such as 5% of a 1M solution of sodium, potassium or lithium hydroxide being useful for this purpose.

As used herein and in the appended claims, it will be appreciated that the term "effective amount" denotes an amount sufficient to provide the recited function.

As will be described more fully hereinafter, the model skin substrate may be prepared simply by adding the ingredients (except crosslinking agent) to water while stirring to form an emulsion. The crosslinker (e.g. formaldehyde) is then added to the emulsion to convert the water-soluble albumin macromolecules to a water-swellable, but insoluble proteinaceous matrix.

A critical aspect of this invention is the provision of a surface for the model skin whose general chemical and physical properties reflect those reported for, or commonly observed for in vivo skin. To accomplish this, the aforementioned formulation is provided whose contact angles with liquids are similar to those measured on human skin. As is known, contact angles of liquids on surfaces are a measure of the liquid's ability to wet that surface, which in turn is governed by the polar and dispersive intermolecular forces acting at the interface. The topographical aspects of skin are approximated utilizing what is referred to in the art as a silicone elastomer replication technique which will be described hereinafter.

Protein/glyceridic ester Ratio

As mentioned previously, the ratio of protein to glyceridic ester in the model skin formulation is from about 2:1 to about 4:1. This fairly narrow range is critical. The wetting of surfaces is known to be controlled by a combination of polar and dispersive forces acting at the solid/liquid interface. By determining the contact angles of two liquids whose surface tensions have been characterized in terms of their polar ($\gamma_L P$) and dispersive ($\gamma_L D$) components, the corresponding components of the solid's surface tension ($\gamma_S P$ and $\gamma_S D$) can be evaluated using the analysis of Wu (see, for example, Wu, S., J. Polymer Sci., Part C, 34, 19 (1971).

$$\gamma_L P + \gamma_L D = \gamma_L$$

$$\gamma_S P + \gamma_S D = \gamma_S$$

When a drop of liquid is placed on a solid, an equilibrium is established which is governed by the intensity of molecular forces which act, on the one hand, between the molecules of the liquid, and, on the other, between the molecules of the liquid and the solid. This equilibrium will determine the angle the drop of liquid makes with the solid surface, and is described by the Young equation:

$$\gamma_{SA} = \gamma_{SL} + \gamma_{LA} \cos\theta$$

where $\gamma_{SA}$ = solid/vapor (air) surface tension
$\gamma_{LA}$ = liquid/vapor (air) surface tension
$\gamma_{SL}$ = solid/liquid surface tension To a first approxmiation, intermolecular forces may be separated into dispersive and polar components. Using the reciprocal mean for both the dispersive and polar interactions, the solid/liquid surface tension (in this case the interfacial tension) may be expressed as:

$$\gamma_{SL} = \gamma_{SA} + \gamma_{LA} - \frac{4\gamma_{SA}^d \gamma_{LA}^d}{\gamma_{SA}^d \gamma_{LA}^d} - \frac{4\gamma_{SA}^p \gamma_{LA}^p}{\gamma_{SA}^p \gamma_{LA}^p}$$

Combination of the Young equation with the above expression yields:

$$\gamma_{LA}(\cos\theta + 1) = \frac{4\gamma_{SA}^d \gamma_{LA}^d}{\gamma_{SA}^d \gamma_{LA}^d} + \frac{4\gamma_{SA}^p \gamma_{LA}^p}{\gamma_{SA}^p \gamma_{LA}^p}$$

By substituting the contact angle cosines of two liquids whose dispersive and polar contributions to their surface tensions are known ($\gamma_{LA}^d$ and $\gamma_{LA}^p$), simultaneous solution of the last expression will yield values of $\gamma_{SA}^d$ and $\gamma_{SA}^p$ from which the ratio $\gamma_{SA}^d$ and $\gamma_{SA}^p$ can be calculated.

A Zisman plot was constructed for the model skin surface by measuring the contact angle of a series of liquids against the model skin surface. A value of 35.8 dynes/cm was obtained, which, considering the various complex factors involved, is reasonable for the model skin surface.

It has been well established that human skin presents a hydrophobic surface. By measuring the contact angles of water and diiodomethane against various model skin candidates having varying protein/glyceridic ester ratios, the appropriate ratio can be determined.

While, as mentioned, ratios on the order of 2:1 to 4:1 can be employed, a ratio of about 3.3:1 results in a model skin surface which, when analyzed by the contact angle method, provides the optimum $\gamma_{LD}/\gamma_{LP}$ ratio of 1.58. This ratio is in agreement with the value of 1.53 reported for in vivo human skin. Accordingly, this ratio of 3.3:1 is considered to be optimum as representing the surface energetics of human skin.

The Zisman plot is described by the equation:

$$\cos \Theta = 1 + m(_{LA} - c)$$

where
   m = the slope of the line
   C = critical surface tension of solid

As can be seen, liquids with surface tensions equal to or smaller than $c$ will spread indefinitely on the solid surface, while liquids with greater surface tensions will make a finite contact angle.

Water Content

The state of hydration of the human stratum corneum depends on the local relative humidity. Because the outermost and bottom layers reside in quite different environments, a gradient in water concentration exists within the stratum corneum. An estimate of 17 and 41 percent for the top and bottom layers respectively under temperate conditions has previously been reported by R. J. Scheuplein and I. H. Bank in *Physiol, Rev.*, 51, 702, (1971). Hydration under moist conditions will markedly increase these values, challenging the performance of adhesives designed for wet environments.

Accordingly, it will be appreciated that the water content of the model skin must be capable of variation to provide a test substrate for testing the adhesive performance under the variations in moisture content of the human skin to which adhesion is contemplated. The present invention provides the capability of having various model skin matrices with varying water contents simulating those of in vivo human skin.

Analysis of 40 mg. pieces prepared in accordance with this invention and dried under ambient conditions indicated water contents of between 9.5 and 10.3 percent. However, this water content can be varied in a predictable manner by allowing the model skin to equilibrate in constant temperature-humidity chambers. Storage at 97° F. and 100% relative humidity for 24 hours, for example, resulted in water contents of between 26.3 and 27.1 percent. A faster, but less precise method of increasing water content is to submerge model skin matrices in water for fixed periods of time, followed by thorough blotting.

The results of these procedures are illustrated in the following table.

TABLE I

| Percentage Water contained in Conditioned MSS | | |
|---|---|---|
| Conditioning | | Number of Trials |
| Ambient | 10.7 ± 0.4 | 6 |
| 100% RH, 98° F., 24 hrs | 26.3 ± 1.2 | 3 |
| 100% RH, 98° F., 5 days | 27.0 ± 1.6 | 3 |
| 5 seconds submerged | 29.6 ± 3.7 | 3 |
| 10 seconds submerged | 34.1 ± 1.7 | 4 |
| 15 seconds submerged | 40.6 ± 2.8 | 7 |
| 20 seconds submerged | 43.1 ± 2.9 | 6 |

Topography

The complexity of skin is further enhanced by the presence of elevations and depressions forming regions of coherent and noncoherent topography. For a model skin to simulate natural skin for purposes of testing in accordance with the task of this invention, it follows that the model skin must also simulate the topography of natural skin.

This may be readily accomplished utilizing the silicone elastomer replication technique which is described, for example, by J. M. Facq, *J. Soc. Cosmet. Chem.* 15, 87 (1964). In accordance with this replication procedure, a mixture of an elastomer precursor and catalyst, e.g. "Silflo" (trademark of Davis, Ltd. of London, England) silicone rubber thinner and catalyst, is employed to make a negative mold or impression of the skin in much the same manner as a dentist would make an impression within the oral cavity for dental restoration procedures. A stirred mixture of elastomer precursor and catalyst is poured rapidly onto the region of the skin selected for replication. Following complete cure, the elastomer is carefully removed from the skin to provide a negative mold which can be employed repeatedly as the substrate for casting the model skin formulation of this invention to provide a model skin which, upon removal from the mold, has one surface corresponding to the mold topography and, accordingly, to the topography of the skin portion utilized to prepare the mold.

Replicas prepared in this manner will vary markedly depending upon the individual and the site of replication. It has been found that the inner forearm provides a convenient area affording model skin surface area yields suitable for adhesion testing. [Accidental and unwanted transfer of small amounts of silicone material to the model skin was ruled out by comparison of the contact angles of water and diiodomethane when model skin surfaces were made adjacent to silicone and a surface such as Mylar.]

The novel model skins of this invention may be made by first forming an emulsion consisting essentially of: (1) from about 85 to about 90 percent by weight of water; (2) from about 8 to about 13 percent by weight of the water-soluble proteinaceous material; and (3) from about 2 to about 4 percent by weight of the triglyceride, the ratio by weight of proteinaceous material to triglyceride being from about 2:1 to about 4:1, as heretofore mentioned, and most preferably on the order of 3:1 to about 3.5:1. [Any other desired reagents to be included, e.g. effective amounts of a bacterial growth inhibitor and/or reagent for preventing phase separation will also be included at this time.] By the way of illustration, the proteinaceous material (e.g. gelatin) may be added to water heated to about 45°–50° C. while stirring well. While maintaining this temperature, a bacterial growth inhibitor, alkali metal hydroxide solution (for preventing phase separation, and then the triglyceride or other ester may then be added in that order, while stirring well.

The crosslinker is then added and the resulting mixture is then quickly poured into the replication mold, as described above. The cured mass is allowed to dry under ambient conditions. After about 24 hours, the model skin is carefully removed from the mold to provide a model skin exhibiting human skin topography on one surface.

The following Examples show by way of illustration and not by way of limitation the practice of this invention.

EXAMPLE 1

10.0 grams of granular porcine skin gelatin, 225 bloom, were dissolve in 83.0 grams of water at 50° C. while stirring. To prevent bacterial contamination, 0.05 gm of propylparaben was then dissolved in the resulting warm gelatin solution. 4.5 cc of IM sodium hydroxide followed by 3.0 grams of G2 (the formula of which was previously described) were then added. The addition of the alkali and G2 resulted in a stable, white emulsion. A negative mold was previously made by mixing one part of "Silflo" catalyst with 15 parts of the silicone precursor, stirring rapidly in view of the fact that setting will begin in about one minute. The catalyzed rubber mix was then poured onto the inner forearm and worked briefly with a spatula to release any air bubblers which may be entrapped at the skin surface, particularly at follicular openings. After about five minutes, the cured silicone mold was carefully stripped from the skin, washed with mild aqueous detergent and rinsed with distilled water. 3.95 grams of formaldehyde were added to the previously prepared emulsion to convert the water soluble gelatin macromolecules to water-swellable, but water-insoluble proteinaceous matrix material. Following the aldehyde crosslinker addition, the resulting mixture was then poured into the negative mold (as prepared above) and allowed to set and dry under ambient conditions. After about 24 hours, it was carefully removed from the mold.

EXAMPLE 2

For comparative testing against the model skin having human skin topography as prepared in Example 1, the Example was repeated except that the formulation with added crosslinker was poured onto a smooth Mylar substrate. Upon drying and stripping, a test matrix having a smooth surface was provided.

For testing, the model skin may be adhesively secured to a suitable test panel, e.g. a steel test panel approximately 6"×2"×1/16". In the case of a model skin having human skin topography on one (the test) surface, it will be appreciated that the opposed (smooth) surface will be the one so adhered. With a comparative skin such as was prepared in Example 2, the smooth surface facing the Mylar substrate is used for testing and the opposed surface will be the one so adhered.

In order to conduct comparative adhesion studies, four adhesive tapes were used, three of which were commercially available, the fourth being an experimental one intended for use under moist conditions. These fur tapes are set forth in the following table.

TABLE II

| | Medical Tapes Tested | |
|---|---|---|
| Table Adhesive | Backing | Use |
| I acrylic | polyvinyl chloride | finger bandages - general |
| II rubber | polyvinyl chloride | finger bandages - general |
| III rubber | woven cotton | general purpose support strapping |
| IV acrylic | polyvinyl chloride | finger bandages - moist conditions |

Each of the above tapes had an adhesive thickness of about 1.7 mils. The four tapes were subjected to standard peel adhesion studies on steel, in vivo human skin, the smooth "model skin" prepared in Example 2, and with the model skin having human skin topography, as prepared in Example 1 with both 10% and 26% water content.

These results of these studies are set forth in Table III, below.

TABLE III

| | 180° Peel Adhesions of Medical Tapes[a,b] | | | | | |
|---|---|---|---|---|---|---|
| Tape | Steel | Human | Smooth MSS 10% Water | Smooth MSS 26% Water | Replica MSS 10% Water | Replica MSS 26% Water |
| I | 296 ± 12 | 82 ± 12 | 271 ± 20 | 137 ± 13 | 59 ± 46 | 40 ± 38 |
| II | 338 ± 11 | 58 ± 10 | 254 ± 18 | 146 ± 20 | 69 ± 18 | 32 ± 20 |
| III | 205 ± 2 | 60 ± 7 | 196 ± 11 | 186 ± 21 | 61 ± 13 | 29 ± 3 |
| IV | 521 ± 56 | (480 ± 40) | 474 ± 46 | 208 ± 5 | 144 ± 80 | 113 ± 50 |

[a]values in grams/cm
[b]50.8 cm/minute peel rate
MSS = Model Skin Surface

The above data denotes an average for twelve subjects for the human studies; and an average for model skin replicas from three subjects.

The data set forth in Table III indicate how adhesion to steel is a poor indicator or benchmark for trends or anticipated adhesion in human wear testing. Not only are the values many times higher on steel relative to the average (12 subjects) for the human test panel, but no clear trend in order of adhesion is observable.

Dermal roughening (providing in vivo skin topography) of the model skin resulted in peel adhesions which were comparable to human results, while the smooth model skin (as prepared in Example 2) did not. Because the replica values were derived from replica molds made from only 3 subjects, they carry a relatively large standard deviation. Increasing the number of different replicas would clearly reduce this standard deviation.

In developing adhesives for various special conditions, it is frequently not possible to obtain rapid medical clearance for human screening tests. An example of this was encountered during the development of the "moist skin" adhesive IV. The model skin of this invention with the enhanced 26% water content proved useful as a screening device during this program. Table III shows that while Tapes I, II and III fell to unacceptable values, Tape IV maintained good adhesion to the "moist skin" test surface.

From the foregoing description, including the test data, it will be seen that the present invention provides a very useful model skin for laboratory screening of adhesive candidates for use of human skin. With the use of this laboratory screening aid, actual results of humans may be predicted.

Since certain changes may be made without departing from the scope of the invention herein involved, it is intended that all matter contained in the above description shall be interpreted as illustrative and not in a limiting sense.

What is claimed is:

1. A model skin substrate adapted for screening testing of adhesion of adhesives to human skin, said model skin substrate being characterized as being water-swellable and water-insoluble, said substrate being further characterized in that the major surface thereof for testing possesses human skin topography, said substrate consisting essentially of:
   (1) water in an adjustable amount ranging from about 8 percent to about 45 percent by weight based upon the total weight of said substrate;
   (2) water-soluble proteinaceous material which has been crosslinked to render it water-insoluble and water-swellable; and (3) di- or triglyceridic ester of a $C_{12}$ or greater fatty acid, said proteinaceous material and glyceridic ester being the remaining percentage of essential material in said substrate, the ratio by weight of proteinaceous material to glyceridic ester being from about 2:1 to about 4:1.

2. A model skin substrate as defined in claim 1 wherein said glyceride ester is triglyceride.

3. A model skin substrate as defined in claim 1 wherein said water-soluble proteinaceous material is selected from the group consisting of gelatin, water-soluble collagen, water-soluble borine globulin, polylysine, polyamino acid copolymers and polyamino acid terpolymers.

4. A model skin substrate as defined in claim 3 wherein the degree of crosslinking of said water-soluble proteinaceous material is not greater than about 95 percent.

5. A model skin substrate as defined in claim 1 wherein said ratio is from about 3:1 to about 3.5:1.

6. A model skin substrate as defined in claim 1 which further includes an effective amount of a bacterial growth inhibitor.

7. A model skin substrate as defined in claim 1 wherein said water-soluble proteinaceous material in gelatin and said ester is a triglyceride.

8. A model skin substrate adapted for in vitro screening of adhesives contemplated for application to human skin, said model skin substrate being characterized as being water-swellable and water-insoluble, said substrate being further characterized in that one major surface thereof possesses human skin topography, said substrate consisting essentially of:
   (1) from about 8 to about 45 percent by weight of water based upon the total weight of essential components of said substrate;
   (2) water-soluble gelatin which has been crosslinked to render it water-insoluble and water-swellable, the degree of crosslinking being no greater than about 95 percent; and
   (3) triglyceridic ester of a $C_{12}$ or greater fatty acid, said crosslinked gelatin and triglyceride ester together with said water content being the essential components of said substrate, the ratio by weight of gelatin to ester being from about 2:1 to about 4:1.

9. A model skin substrate as defined in claim 8 wherein said water content is from about 9.5 to about 10.3 percent by weight.

10. A model skin substrate as defined in claim 8 wherein said ratio is from about 3:1 to about 3 5:1.

* * * * *